(12) United States Patent
Divi et al.

(10) Patent No.: US 8,212,072 B2
(45) Date of Patent: Jul. 3, 2012

(54) PROCESS FOR THE PREPARATION OF PREGABALIN

(75) Inventors: Murali Krishna Prasad Divi, Hyderabad (IN); Gundu Rao Padakandala, Hyderabad (IN); Mysore Aswatha Narayana Rao, Hyderabad (IN); Srinivasan Subramanian Kuduva, Hyderabad (IN)

(73) Assignee: Divi's Laboratories, Ltd. (IN)

( * ) Notice: Subject to any disclaimer, the term of this patent is extended or adjusted under 35 U.S.C. 154(b) by 0 days.

(21) Appl. No.: 12/983,550

(22) Filed: Jan. 3, 2011

(65) Prior Publication Data

US 2012/0041212 A1    Feb. 16, 2012

(30) Foreign Application Priority Data

Aug. 13, 2010 (IN) .......................... 2339/CHE/2010

(51) Int. Cl.
*C07C 229/08* (2006.01)
*C07D 207/12* (2006.01)
(52) U.S. Cl. ........................ 562/553; 548/543
(58) Field of Classification Search .................. 562/553; 548/543
See application file for complete search history.

(56) References Cited

U.S. PATENT DOCUMENTS

| 5,563,175 | A | 10/1996 | Silverman et al. |
| 5,599,973 | A | 2/1997 | Silverman et al. |
| 5,616,793 | A | 4/1997 | Huckabee et al. |
| 5,637,767 | A | 6/1997 | Grote et al. |
| 6,046,353 | A | 4/2000 | Grote et al. |
| 7,192,969 | B2 | 3/2007 | Ogino et al. |
| 7,381,747 | B2 * | 6/2008 | Dooley et al. .................. 514/567 |

FOREIGN PATENT DOCUMENTS

| EP | 0641330 | B1 | 10/2001 |
| EP | 1250311 | B1 | 10/2002 |
| EP | 2017273 | * | 1/2009 |
| EP | 2017273 | A1 | 1/2009 |
| WO | 2009053446 | A2 | 4/2009 |

OTHER PUBLICATIONS

Glenn M. Sammis and Eric N. Jacobsen, Highly Enantioselective, Catalytic Conjugate Addition of Cyanide to a,B-Unsaturated Imides, Department of Chemistry and Chemical Biology, Harvard University, Cambridge, Massachusetts 02138, J. Am, Chem. Soc. 2003, 125, 4442-4443.

Roberta Galeazzi, Giovanna Mobbili and Mario Orena, From 3-Aza-2-Oxobicyclo[3.1.0]Hexane to Enantiopure Disubstituted Cyclopropane: A Convenient Approach to CIS-2,3-Methano-GABA, Tetrahedron, Asymmetry, vol. 8. No. 1, pp. 133-137, 1997.

Veronica Rodriguez, Leticia Quintero and Fernando Sartillo-Piscil, Stereoselective 5-Exo-Trig Radical Cyclizatio in the Enantioselective Systhesis of Pregabalin, Tetrahedron Letters 48 (2007) 4305-4308.

Search Report dated Nov. 7, 2011.

Robert Galeazzi, et al. A Convenient Approach to Diastereomerially Pure 1,3,4-Trisubstituted Pyrrolidin-2ones by Intramolecular cyclisation of N-(2-Alken-1-yl)amides Mediated Mn(III). An entry to Both (R)-and(s)-3-Pyrrolidineacetic Acid, Tetrahedron, vol. 52, No. 3 pp. 1069-1084, 1996.

Veronica Rodriguez, et al. Stereoselective 5-exo-trig radical cyclization in the enantioselective synthesis of Pregabalin, Tetrahedron Letters 48 (2007) 4305-4308.

* cited by examiner

*Primary Examiner* — Robert Havlin
(74) *Attorney, Agent, or Firm* — Caesar, Rivise, Bernstein, Cohen & Pokotilow, Ltd.

(57) ABSTRACT

The present invention provides a new enantioselective method of preparing (S)-3-(aminomethyl)-5-methylhexanoic acid, commonly known as pregabalin. The invention also provides new chiral intermediates useful in the production of pregabalin.

9 Claims, No Drawings

PROCESS FOR THE PREPARATION OF PREGABALIN

CROSS-REFERENCE TO RELATED APPLICATIONS

This application claims priority from India Application Serial No. 2339/CHE/2010, filed on Aug. 13, 2010, entitled Process for the Preparation of Pregablin, which application is assigned to the same assignee as this application and whose disclosure is incorporated by reference herein.

FIELD OF INVENTION

The present invention relates to an enantioselective process for the preparation of (S)-3-(aminomethyl)-5-methylhexanoic acid, commonly known as pregabalin. The invention also relates to new chiral intermediates useful in the production of pregabalin.

BACKGROUND OF THE INVENTION

Pregabalin, which is chemically (S)-isomer of 3-(aminomethyl)-5-methylhexanoic acid, also called β-isobutyl-γ-aminobutyric acid or isobutyl-GABA, has the following chemical structure:

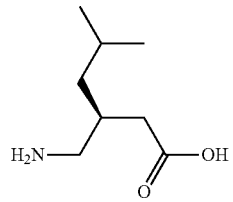

This compound is disclosed in EP641 330 B1 and marketed with the trade name Lyrica®. Pregabalin is useful as a therapeutic agent for the treatment of pain, epilepsy, convulsions, psychiatric disorders, attention deficit, hypersensitivity disorder, anxiety and mood disorders. It has been discovered that the anticonvulsant effect of pregabalin is dependent on its stereochemistry. The anticonvulsant effect of the racemic form of pregabalin is primarily attributable to the (S)-enantiomer, i.e., pregabalin. Pregabalin shows better anticonvulsant activity than its (R)-stereoisomer (Yuen et al., *Bioorganic & Medicinal Chemistry Letters*, 1994, 4, 823).

Several methods have been reported for the preparation of pregabalin. Typically racemic pregabalin is prepared and later resolved into (R) and (S) isomers using classical methods. First racemic pregabalin was described in *Synthesis*, 1989, 953. This method requires hazardous chemicals such as nitromethane and results in nitro intermediates which are unstable. U.S. Pat. No. 5,563,175 describes the synthesis of racemic pregabalin using an azide intermediate. U.S. Pat. No. 5,637,767 describes the synthesis of racemic pregabalin followed by resolution of S-isomer using mandelic acid. U.S. Pat. No. 6,046,353 describes the synthesis of racemic pregabalin through malonate salt. U.S. Pat. No. 5,616,793 describes the synthesis of racemic pregabalin through Hofmann rearrangement and resolution using chiral phenylethylamine.

In pregabalin, the carboxylic acid or amine moiety is not directly attached to an asymmetric carbon atom. Because of this, salt formation with a resolving agent is not selective and efficient. It requires several repeated crystallizations to obtain the desired enantiomeric purity. Further, the unwanted R-enantiomer cannot be efficiently racemised and recycled. It has to be ultimately discarded as waste adding to the production cost.

The direct synthesis of chirally pure S-pregabalin using Evan's chiral auxiliary (Scheme 1) is described in U.S. Pat. No. 5,599,973. The cost and recycling of the chiral auxiliary makes the process commercially unattractive.

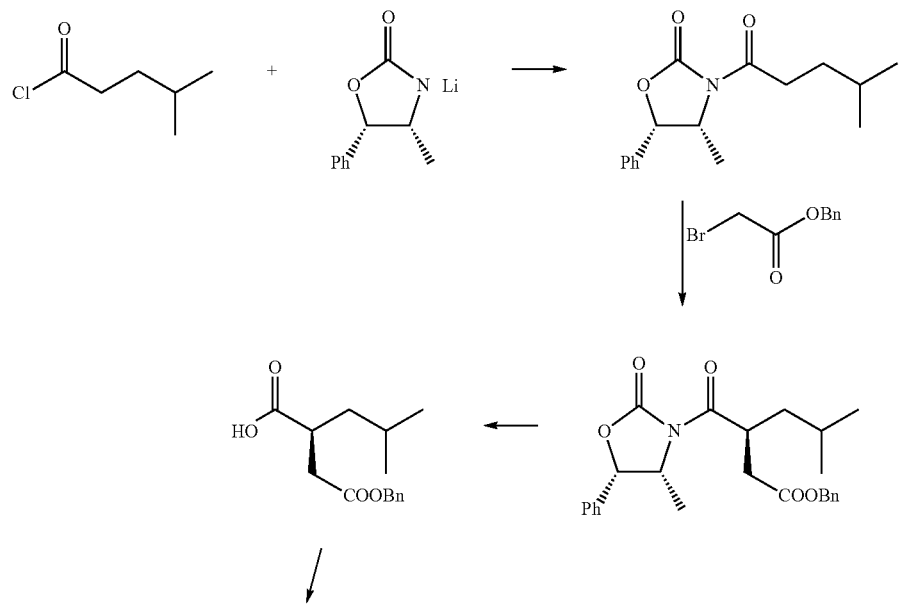

Scheme 1

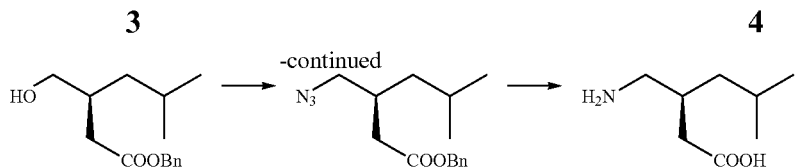

Jacobsen's group reported a chiral synthesis of pregabalin using chiral aluminum salen catalyst and trimethylsilyl cyanide (*J. Am. Chem. Soc.,* 2003, 125, 4442-4443). Although the method gives pregabalin with a high enantiomeric purity, it is not suitable for large scale industrial synthesis because of the high cost of reagents such as chiral aluminum salen catalyst and trimethylsilyl cyanide.

Another chiral synthesis of pregabalin is reported (A. Armstrong. et al. *Synlett* 2006, 10, 1589-1591), which uses samarium (III) isopropoxide as a catalyst. This method is also not suitable for industrial scale synthesis because of the expensive reagents.

EP 1 250 311 discloses the preparation of pregabalin using asymmetric hydrogenation of a cyano substituted olefin. It uses bisphosphine ligands such as (R, R)-Me-DUPHOS. The process also involves the use of carcinogenic acrylonitrile and highly toxic carbon monoxide under high pressure.

Thus, there is a need for the development of a cost effective enantioselective process which is suitable for industrial scale and free from some of the disadvantages mentioned in the above prior art.

SUMMARY OF THE INVENTION

The present invention describes a process for the preparation of the (S)-isomer of 3-(aminomethyl)-5-methylhexanoic acid (pregabalin) from an intermediate I where R is alkyl or substituted alkyl group and the asymmetric carbon C-4 of pyrrolidinone has (S) configuration. The intermediate I can be prepared as given in Scheme 2 from a known alcohol (*Tetrahedron asymmetry,* 1997, 8, 133-138; U.S. Pat. No. 7,381,747 B2.)

In another embodiment, the present invention also describes intermediates II, IIIa & IIIb, IVa & IVb which are novel and not reported in the literature until now.

The process for the preparation of pregabalin comprises, alkylation of the intermediate I, to obtain a tertiary alcohol II.

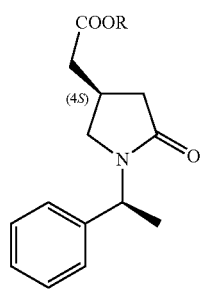

I

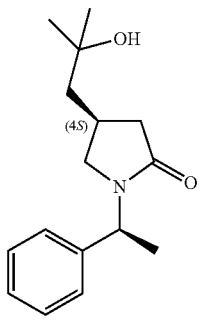

II

The tertiary alcohol II, on dehydration, gives (4S)-4-(2-methylprop-1-enyl)-1-[(1S)-1-phenylethyl]pyrrolidin-2-one IIIa and/or (4R)-4-(2-methylprop-2-enyl)-1-[(1S)-1-phenylethyl]pyrrolidin-2-one IIIb:

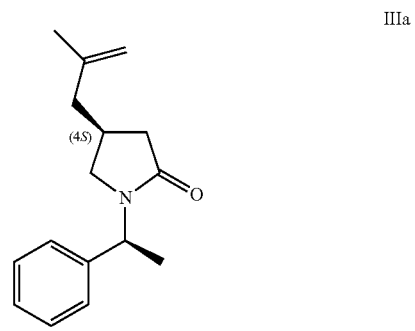

IIIa

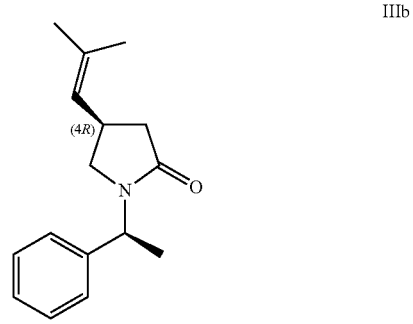

IIIb

Deprotection of the amide nitrogen of IIIa and/or IIIb gives, (4S)-4-(2-methylprop-1-enyl)pyrrolidin-2-one IVa and/or (4R)-4-(2-methylprop-2-enyl)pyrrolidin-2-one IVb:

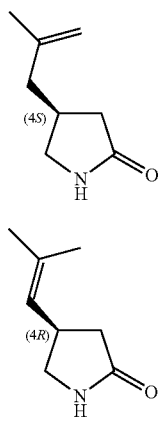

IVa

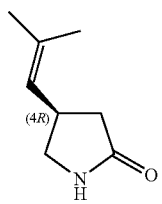

IVb

Hydrogenation of the lactam IVa and/or IVb results in pregabalin lactam V. Since both isomers, IVa and IVb, give the same lactam V, their ratio will not influence the stereochemistry of the lactam V, at position 4.

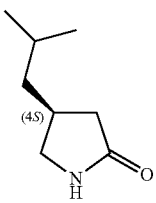

V

Hydrolysis of the lactam V results in pregabalin with high enantiomeric purity.

The advantage of the present process is that it gives the required (S)-isomer. Obtaining the (S)-isomer from a racemic mixture by resolution is difficult, cumbersome and requires repeated crystallizations to obtain the required enantiomeric purity. Further, the present process does not require hazardous compounds such as nitromethane or expensive chiral auxiliaries.

DETAILED DESCRIPTION OF THE INVENTION

According to the present invention, there is provided a process for the enantioselective preparation of (S)-3-(aminomethyl)-5-methylhexanoic acid (pregabalin) which comprises:

a) converting a compound of the formula (I) where, R is alkyl or substituted alkyl group and the asymmetric carbon C-4 of pyrrolidinone has (S) configuration,

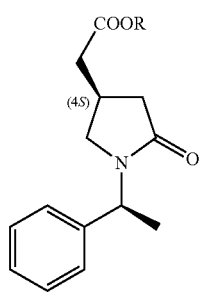

I to a tertiary alcohol intermediate of the formula (II):

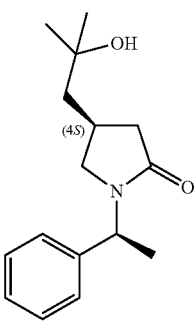

II dehydration of the tertiary alcohol intermediate of the formula (II) to yield an alkene intermediate, (4S)-4-(2-methylprop-1-enyl)-1-[(1S)-1-phenylethyl]pyrrolidin-2-one IIIa and or (4R)-4-(2-methylprop-2-enyl)-1-[(1S)-1-phenylethyl]pyrrolidin-2-one IIIb b)

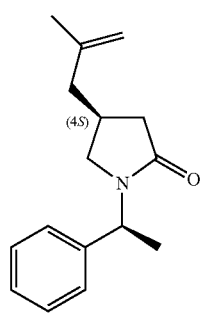

IIIa

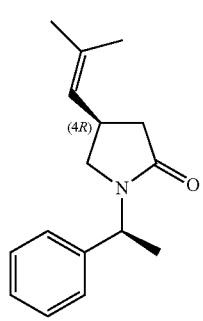

IIIb c) conversion of the alkene intermediate of the formula IIIa and/or IIIb to (4S)-4-(2-methylprop-1-enyl)pyrrolidin-2-one IVa and or (4R)-4-(2-methylprop-2-enyl)pyrrolidin-2-one IVb

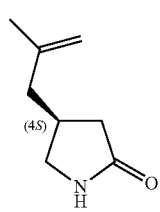

IVa

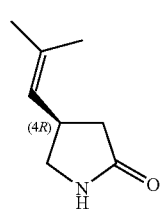

d) hydrogenation of lactam of the formula IVa and/or IVb to yield pregabalin lactam of the formula V:

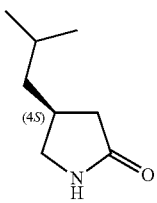

e) hydrolyzing the lactam of the formula V to yield pregabalin.

The ester of formula I is a diastereoisomer having (S)-configuration both at carbon (4) of the pyrrolidinone ring and at the asymmetric carbon attached to nitrogen. This ester of formula (I) can be prepared as given in Scheme 2. The starting alcohol, (S)-4-(hydroxymethyl)-1-(S)-1-phenylethyl)pyrrolidine-2-one in Scheme 2 may be prepared by any of the known methods, as for example, *Tetrahedron asymmetry*, 1997, 8, 133-138; U.S. Pat. No. 7,381,747 B2.

Scheme 2

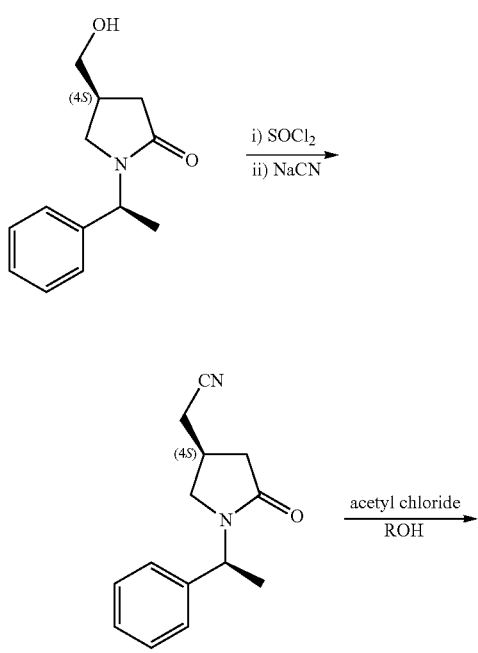

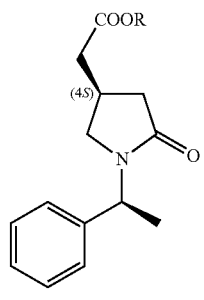

The alcohol, (S)-4-(hydroxymethyl)-1-((S)-1-phenylethyl)pyrrolidine-2-one, is treated with a chlorinating agent such as thionyl chloride to obtain a chloro compound followed by treatment with alkali cyanide to give a nitrile derivative. Treating the nitrile derivative with acetylchloride in alcohol results in the ester of formula I. Ester I with R-configuration at the asymmetric carbon attached to nitrogen is described in U.S. Pat. No. 7,192,969 B2. The ester I undergoes a Grignard reaction with methyl magnesium halide to give compound II. The halide can be chloro or bromo, preferably chloro, and the solvent used for the reaction may include, but is not limited to anhydrous solvents such as diethyl ether, diisopropyl ether, methyl t-butyl ether, tetrahydrofuran and may be used alone or in combination with two or more thereof, but also with other solvents such as toluene, hexane, heptane. The reaction temperature may vary depending on the solvent, ranging from −70 to 100° C., preferably 30° C. The reaction time may also vary depending on the reaction temperature and the solvent used, ranging from 1 to 18 hours. In addition, methylmagnesium halide is preferably used in an amount of 2 to 10 mole equivalents. One skilled in the art may also carry out the reaction in the presence of any copper compound, for example, of the formula CuY, where Y may be any one of Cl, Br, I, and CN, preferably I. One skilled in the art can utilize other metal based reagents such as methyl lithium, dimethyl zinc, dimethyl cadmium and the like, to prepare compound II. One skilled in the art can also prepare the compound II alternatively from a nitrile derivative by treating with methylmagnesium halide in a Grignard type reaction.

Subsequent dehydration of the compound II results in compound IIIa and/or LB or their mixture. The dehydrating reagents that can be used include but not limited to, para-tolylsulfonic acid, concentrated $H_2SO_4$, phosphorus pentoxide, trifluoroacetic acid, preferably para-tolylsulfonic acid and the solvent used for dehydration may include, but is not limited to toluene, xylene, benzene, heptane, hexane, acetone, ethyl acetate, methyl t-butyl ether, diisopropyl ether, preferably toluene or xylene and more preferably toluene.

Reductive deprotection of the compounds IIIa and IIIb using Birch type reaction results in the compounds IVa and IVb. The reaction is carried out by treating with an alkali metal and liquid ammonia. Alkali metals include sodium or lithium, preferably a sodium metal. Alternatively, one skilled in the art can also use ceric ammonium nitrate or other methods described in the literature for the deprotection.

Pregabalin lactam of the formula V can be easily prepared from the compounds IVa and IVb by hydrogenation using a suitable catalyst known to those skilled in the art. Solvents used for the hydrogenation reaction include polar protic solvents like alcohols, such as methanol, ethanol, isopropanol, or esters such as ethyl acetate, isopropyl acetate, methyl acetate, or aliphatic acids such as formic acid, acetic acid. Solvents may also include nonpolar solvents like aliphatic or aromatic hydrocarbons such as heptane, hexane, pentane, cyclohexane, benzene, toluene, xylene, ethyl benzene, polar aprotic solvents such as dimethylformamide, dimethylacetamide or N-methylpyrrolidone, or mixtures thereof. Suitable temperature for the hydrogenation reaction may range from about 0° C. to the solvent reflux temperature, preferably from about 10 to 50° C., more preferably at about 25° C.

Pregabalin lactam of the formula (V) can be easily hydrolyzed to obtain pregabalin as is known in the literature, for example as described in *Tetrahedron Letters* 2007, 48, 4305-4308 or application WO 2009/053446 A2.

The advantage of the present process is that it gives the required (S)-isomer only and avoids the difficult and cumbersome process of resolving the racemic mixture, which also needs repeated crystallizations to obtain required enantiomeric purity. Further, the present process does not require the hazardous compounds such as nitromethane or expensive chiral auxiliaries.

Thus, the present invention is economical, environmentally benign and well suited for industrial scale.

The details of the present invention are given in the following examples, which are provided to illustrate the invention and should not be construed in any way to limit the scope of the present invention.

EXAMPLES

Synthesis of Ester I

A. Preparation of [(3S)-5-oxo-1-[(1S)-1-phenylethyl]pyrrolidin-3-yl]acetonitrile

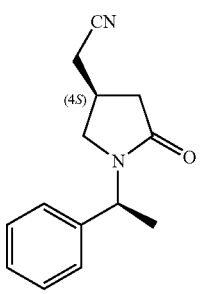

(4S)-4-(hydroxymethyl)-1-[(1S)-1-phenylethyl]pyrrolidin-2-one (*Tetrahedron asymmetry*, 1997, 8, 133-138; U.S. Pat. No. 7,381,747 B2) (25 gm, 0.114 mol) in 150 mL of chloroform was treated drop wise with thionyl chloride (37.2 gm) and refluxed for about 3 hours. After completion of the reaction, solvent was evaporated under vacuum. A dark brown oily chloro derivative was isolated in 100% yield.

The chloro compound obtained as above was taken in DMSO (25 mL) and was added to a solution of sodium cyanide (9 gm, 0.18 mol) in DMSO (100 mL). The reaction mixture was heated to about 150° C. and maintained for about 6 hours. After completion of the reaction, the reaction mixture cooled to 25° C. and poured into 700 gm of crushed ice and extracted with dichloromethane (4×100 mL). The organic layer was washed with dil. HCl solution and then brine solution. The organic phase was dried over $Na_2SO_4$ and the solvent was removed. Dark brown low melting solid nitrile isolated with yield of 22.5 gm (93%). $H^1NMR$ (300 MHz, $CDCl_3$) δ 7.2-7.3 (m, 5H), 5.39-5.46 (q, 1H), 3.02-3.16 (m, 2H), 2.49-2.65 (m, 2H), 2.37-2.42 (m, 2H), 2.18-2.37 (dd, 1H), 1.45-1.47 (d, 3H). $C^{13}NMR$ (75 MHz, $CDCl_3$) δ 16.05, 21.80, 28.5, 36.95, 46.88, 49.14, 60.4, 117.48, 126.04, 127.88, 128.7, 139.45, 172.1.

B.

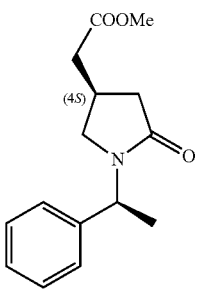

[(3S)-5-oxo-1-[(1S)-1-phenylethyl]pyrrolidin-3-yl]acetonitrile (25 gm, 0.109 mol) in methanol (150 mL) was cooled to about −10 to 5° C. and treated with acetyl chloride (182.9 gm, 2.33 mol) and allowed to warm to 25° C. The reaction mixture was stirred at 25° C. for about 3 days. After completion of the reaction, solvent was evaporated under vacuum and 200 mL of water added to the residue and pH adjusted to neutral using sat.$NaHCO_3$ solution, extracted with dichloromethane (4×100 mL). The organic phase was dried over $Na_2SO_4$ and the solvent was removed. Oily ester I with yield of 24.5 gm (86%) isolated. $H^1NMR$ (300 MHz, $CDCl_3$) δ 7.2-7.3 (m, 5H), 5.41-5.48 (q, 1H), 3.62 (s, 3H), 3.13-3.19 (m, 1H), 2.94-3.0 (m, 1H), 2.54-22.1 (m, 2H), 2.36-2.48 (m, 2H), 2.08-2.18 (q, 1H), 1.45-1.50 (d, 3H). $C^{13}NMR$ (75 MHz, $CDCl_3$) δ 16.11, 28.3, 37.6, 38.36, 47.57, 48.79, 51.72, 127.01, 127.57, 128.54, 139.97, 172.02, 172.98.

Example-1

Synthesis of (4S)-4-(2-hydroxy-2-methylpropyl)-1-[(1S)-1-phenylethyl]pyrrolidin-2-one II

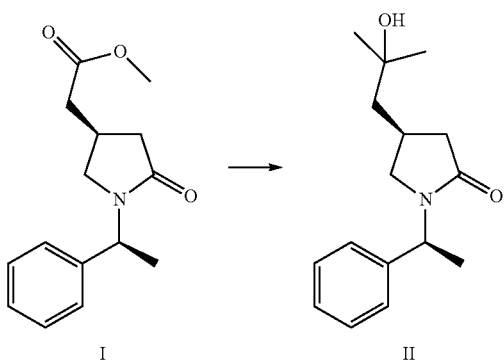

To a solution of compound I (25 gm, 0.0956 mol) in THF (200 mL), methyl magnesium chloride (3 mole solution in THF, 21.4 gm, 0.2868 mol) was added drop wise under nitrogen atmosphere at −10 to 5° C. The resultant reaction mixture was refluxed at about 60 to 70° C. for about 2 to 8 hours and then poured into a 40 mL dil. HCl solution and crushed ice mixture and pH adjusted to 2, extracted with ethyl acetate (3×100 mL), washed with a brine solution, dried and solvent evaporated to yield compound (II) as a dark brown oily material with a yield of 21.6 gm (87%), which was taken to the next stage without further purification. H¹NMR (300 MHz, CDCl₃) δ 7.2-7.35 (m, 5H), 5.42-5.49 (q, 1H), 3.11-3.20 (t, 1H), 2.97-3.08 (t, 1H), 2.36-2.61 (m, 3H), 2.14-2.25 (m, 2H), 1.60-1.67 (d, 2H), 1.48-1.55 (d, 3H), 1.15-1.26 (d, 4H). C¹³NMR (75 MHz, CDCl₃) δ 16.20, 28.7, 30.13, 31.39, 39.61, 47.83, 48.74, 49.24, 70.55, 126.90, 127.53, 128.51, 140.37, 174.01.

Example-2

Synthesis of (4S)-4-(2-methylprop-1-enyl)-1-[(1S)-1-phenylethyl]pyrrolidin-2-one IIIa and or (4R)-4-(2-methylprop-2-enyl)-1-[(1S)-1-phenylethyl]pyrrolidin-2-one IIIb

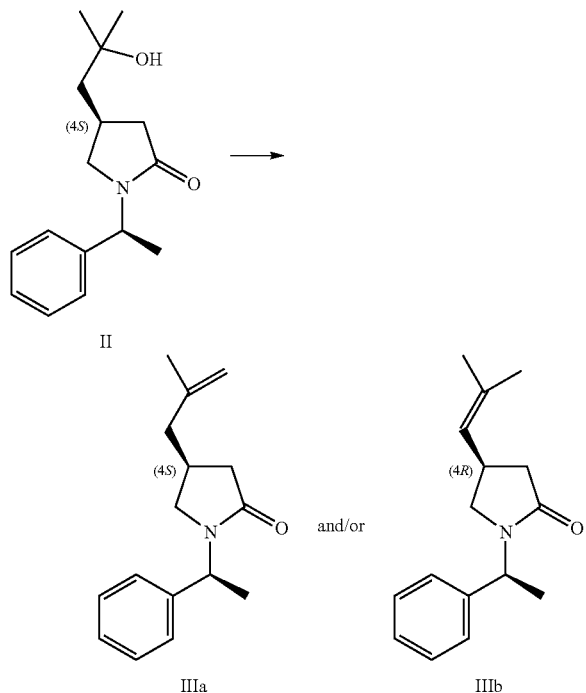

To a solution of compound II (25 gm, 0.0956 mol) in 150 mL of toluene, 2.5 gm of para-toluenesulfonic acid was added. The reaction mixture refluxed at 120° C. using a Dean-Stark apparatus and water collected was removed. After completion of the reaction, the reaction mixture was washed with water and a saturated solution of NaHCO₃. The toluene layer was washed with a brine solution, dried and solvent evaporated to yield mixture of compounds of formula IIIa and IIIb as a dark brown oily material with a yield of 20.0 gm (86%), which was used in the next stage without further purification. H¹NMR (300 MHz, CDCl₃) δ 7.24-7.30 (m, 5H), 5.40-5.43 (q, 1H), [5.0-5.05 (d), 4.7-4.73 (d), 4.6 (s) (mixture of alkene isomer H)], 2.89-3.03 (m, 3H), 2.45-2.54 (m, 2H), 2.03-2.16 (m, 2H), [1.61 (s), 1.51 (s) (mixture of alkene isomer H)], 1.43-1.50 (d, 3H). C¹³NMR (75 MHz, CDCl₃) δ 16.97, 21.16, 24.58, 28.22, 30.1, 36.63, 37.73, 41.84, 46.43, 47.37, 47.79, 111.24, 124.24, 124.62, 125.98, 126.38, 127.16, 127.48, 127.97, 133.00, 139.13, 141.80, 172.68, 172.80.

Example-3

Synthesis of (4S)-4-(2-methylprop-1-enyl)pyrrolidin-2-one IVa and or (4R)-4-(2-methylprop-2-enyl)pyrrolidin-2-one IVb

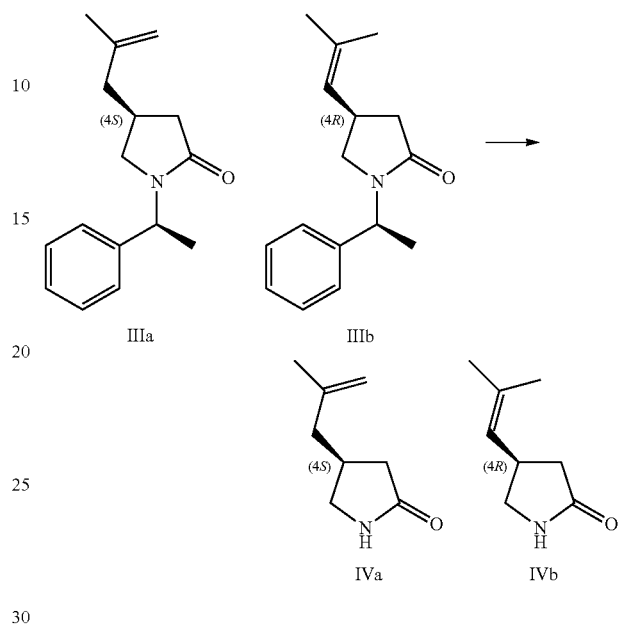

A solution of a mixture of compounds IIIa and IIIb (25 gm, 0.1026 mol) in 100 mL THF was added drop wise to a deep blue color solution of sodium (8.7 gm) in condensed ammonia (150 mL) at −76° C. The reaction mixture was stirred for about 4 hours at −76° C. before the addition of methanol (60 mL). The ammonia was evaporated by allowing the reaction mixture to warm up to RT. The reaction mixture was neutralized with a diluted solution of HCl, extracted with ethyl acetate, dried with Na₂SO₄ and solvent removed under reduced pressure. The residue was purified by high vacuum distillation to get a mixture of IVa and IVb as a low melting solid with a yield of 9.7 gm (67%). H¹NMR (300 MHz, CDCl₃) δ [5.15-5.12 (d), 4.79 (s), 4.70 (s), (mixture of alkene isomer H)], 3.45-3.51 (t, 1H), 3.25-3.33 (m, 1H), 3.02-3.07 (t, 1H), 2.4-2.48 (m, 1H), 1.98-2.17 (m, 3H), 1.64-1.71 (d, mixture of alkene isomer). C¹³NMR (75 MHz, CDCl₃) peaks corresponds to compound of formula IVa: δ 18.01, 25.61, 34.17, 37.59, 48.53, 125.57, 133.91, 178.77, and peaks corresponds to compound of formula IVb: δ 22.26, 32.33, 36.68, 42.89, 47.78, 112.17, 142.89, and 178.67.

Example-4

Synthesis of (4S)-4-isobutylpyrrolidin-2-one V

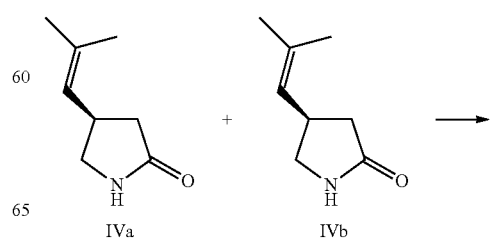

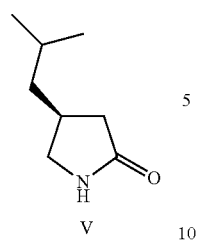

V

To a mixture of compounds IVa and IVb (5 gm, 0.0352 mol) in methanol (100 mL), a 10% Palladium on carbon (0.5 gm) was added and stirred in a hydrogenation unit for about 12 hours. Palladium on carbon was removed by filtering under cellite, and the solvent was evaporated under reduced pressure to obtain compound V as a low melting solid in 99% yield. $H^1$NMR (300 MHz, $CDCl_3$) δ 3.48-3.53 (dd, 1H), 3.02 (t, 1H), 2.37-2.57 (m, 2H), 1.97-2.02 (m, 1H), 1.53-1.60 (m, 1H), 1.33-1.38 (t, 2H), 0.9-0.92 (dd, 6H). $C^{13}$NMR (75 MHz, $CDCl_3$) δ 22.48, 22.67, 26.14, 32.93, 37.5, 43.86, 48.4, 179.0.

Example-5

Synthesis of Pregabalin

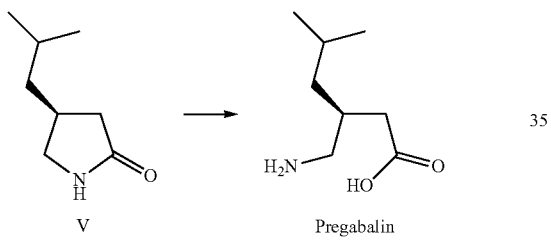

V          Pregabalin

Compound V (12.0 gm, 0.086 mol) was dissolved in 80 mL of 6N HCl and refluxed for 15 hours, then cooled to room temperature. Water was removed under vacuum and the resultant solid product was dissolved in a solution of isopropyl alcohol (50 mL) and water (25 mL). Tributyl amine (22.3 gm) was added to the above mixture and stirred at −10 to 5° C. for 5 hours. The solid material formed was filtered and dried to get pregabalin as a colourless solid with yield of 10 gm (73%) isolated. $H^1$NMR (300 MHz, $D_2O$) δ 3.07-3.09 (d, 2H), 2.51-2.54 (t, 2H), 2.28-2.34 (m, 1H), 1.66-1.73 (m, 1H), 1.28-1.33 (t, 2H), 0.92-0.97 (dd, 6H). $C^{13}$NMR (75 MHz, $D_2O$) δ 21.35, 21.98, 24.38, 30.89, 36.23, 40.18, 43.06, 176.71. Chemical HPLC purity: 99.7%, Chiral HPLC Purity: 99.99%.

Without further evaluation the foregoing will so fully illustrate our invention that others may, by applying current or future knowledge, adopt the same for use under various conditions of service.

We claim:

1. A method of preparing pregabalin which comprises:
   a) converting a compound of the formula (I) where R is alkyl or substituted alkyl group and the asymmetric carbon C-4 of pyrrolidinone has an (S) configuration,

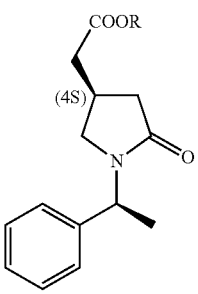

I to a tertiary alcohol intermediate of the formula (II):

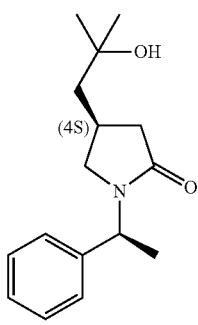

II b) dehydration of the tertiary alcohol intermediate of the formula (II) to yield an alkene intermediate: (4S)-4-(2-methylprop-1-enyl)-1-[(1S)-1-phenylethyl]pyrrolidin-2-one IIIa and/or (4R)-4-(2-methylprop-2-enyl)-1-[(1S)-1-phenylethyl]pyrrolidin-2-one IIIb or a mixture thereof:

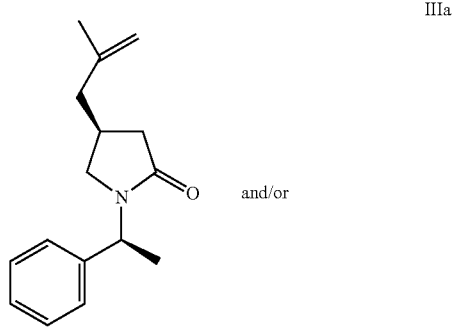

IIIa and/or

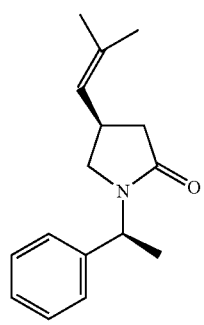

IIIb c) conversion of the alkene intermediate of the formula IIIa and/or IIIb to (4S)-4-(2-methylprop-1-enyl)pyrrolidin- 2-one IVa and or (4R)-4-(2-methylprop-2-enyl)pyrrolidin-2-one or a mixture thereof

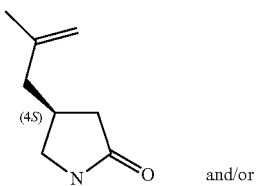

and/or

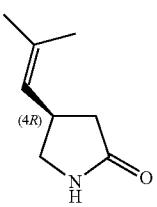

d) hydrogenation of lactam of the formula IVa and/or IVb or a mixture thereof to yield pregabalin lactam of the formula (V):

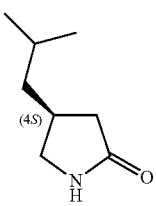

e) hydrolyzing the lactam of the formula (V) to yield pregabalin

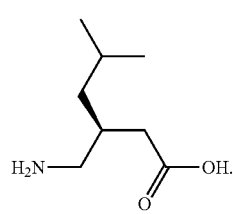

2. The process as described in claim 1 step (a), wherein the compound (I) is treated with a methyl magnesium halide in one or more solvents from the group consisting of diethyl ether, diisopropyl ether, methyl t-butyl ether and tetrahydrofuran, to yield a tertiary alcohol of the formula (II)

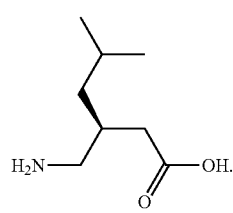

3. The process as described in claim 1 step (a), wherein the compound (I) is treated with a methyl magnesium halide in one or more solvents suitable for use in a Grignard reaction.

4. The process as described in claim 1 step (b), wherein the dehydration step comprises treating the tertiary alcohol intermediate (II) with an acid to obtain an alkene (IIIa) and/or (IIIb) or a mixture thereof.

5. The process as described in claim 4 wherein the acid is para-tolylsulphonic acid.

6. The process as described in claim 1 step (c), wherein the compound (IIIa) and/or (IIIb) or a mixture thereof is subjected to reduction using sodium or lithium metal in ammonia to yield a lactam (IVa) and/or (IVb) or a mixture thereof.

7. A compound of the formula (II):

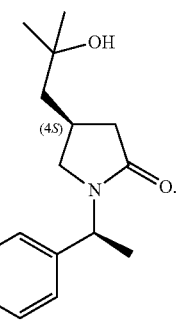

8. Compound (4R)-4-(2-methylprop-2-enyl)-1-[(1S)-1-phenylethyl]pyrrolidin-2-one IIIb:

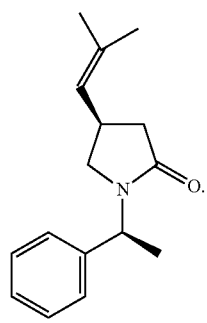

9. Compound (4R)-4-(2-methylprop-2-enyl)pyrrolidin-2-one IVb:

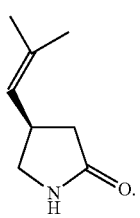

* * * * *